(12) United States Patent
Audiere et al.

(10) Patent No.: US 11,246,570 B2
(45) Date of Patent: Feb. 15, 2022

(54) PROBE FOR TRANSIENT ELASTOGRAPHY

(71) Applicant: ECHOSENS, Paris (FR)

(72) Inventors: Stéphane Audiere, Paris (FR); Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 314 days.

(21) Appl. No.: 16/345,387

(22) PCT Filed: Oct. 26, 2017

(86) PCT No.: PCT/EP2017/077417
§ 371 (c)(1),
(2) Date: Apr. 26, 2019

(87) PCT Pub. No.: WO2018/078002
PCT Pub. Date: May 3, 2018

(65) Prior Publication Data
US 2019/0261951 A1  Aug. 29, 2019

(30) Foreign Application Priority Data
Oct. 28, 2016  (EP) .................................... 16196165

(51) Int. Cl.
*A61B 8/08*   (2006.01)
*G01N 29/04*  (2006.01)
(Continued)

(52) U.S. Cl.
CPC .............. *A61B 8/485* (2013.01); *A61B 8/08* (2013.01); *A61B 8/429* (2013.01); *A61B 8/4209* (2013.01);
(Continued)

(58) Field of Classification Search
None
See application file for complete search history.

(56) References Cited

U.S. PATENT DOCUMENTS 4,213,462 A * 7/1980 Sato .................... A61B 1/2736
                                                                 356/434
8,333,704 B2  12/2012  Anthony et al.
(Continued)

FOREIGN PATENT DOCUMENTS

EP    1 169 636 A1    1/2002
EP    1 531 733 A2    5/2005
(Continued)

OTHER PUBLICATIONS

Mellema et al., "Probe Oscillation Shear Elastography (PROSE): A High Frame-Rate Method for Two-Dimensional Ultrasound Shear Wave Elastography" IEEE Transactions on Medical Imaging, vol. 35, No. 9, Sep. 2016 (Year: 2016).*
(Continued)

*Primary Examiner* — Colin T. Sakamoto
(74) *Attorney, Agent, or Firm* — Pillsbury Winthrop Shaw Pittman LLP (57) ABSTRACT

A probe for transient elastography includes a probe casing, at least one ultrasound transducer having a symmetry axis, a vibrator located inside the probe casing, a position sensor coupled to the probe casing, the position sensor being arranged to measure the displacement of the probe, wherein the vibrator is arranged to induce a movement of the probe casing along a predefined axis, the predefined axis being the symmetry axis of the ultrasound transducer. The ultrasound transducer is bound to the probe casing with no motion of the ultrasound transducer with respect to the probe casing, and the probe includes a feedback circuit including the position sensor and a control loop and configured to use the displacement of the probe as a feedback signal and to control the movement of the vibrator inside the probe casing and the shape of a low frequency pulse applied by the probe.

13 Claims, 6 Drawing Sheets

(51) Int. Cl.
  *G01S 7/52* (2006.01)
  *A61B 8/00* (2006.01)
(52) U.S. Cl.
  CPC .............. *A61B 8/44* (2013.01); *A61B 8/4444* (2013.01); *G01N 29/045* (2013.01); *G01S 7/52042* (2013.01)

(56) References Cited

U.S. PATENT DOCUMENTS

| | | | |
|---|---|---|---|
| 9,538,982 B2 | 1/2017 | Anthony | |
| 10,063,369 B1 | 8/2018 | Murphy | |
| 10,575,780 B2 | 3/2020 | Van Den Ende | |
| 2005/0085728 A1 | 4/2005 | Fukuda | |
| 2005/0119568 A1* | 6/2005 | Salcudean | A61B 8/485 600/437 |
| 2005/0203398 A1 | 9/2005 | Sandrin et al. | |
| 2012/0123263 A1* | 5/2012 | Osaka | A61B 5/0051 600/438 |
| 2012/0172710 A1 | 7/2012 | Anthony | |
| 2012/0316407 A1 | 12/2012 | Anthony et al. | |
| 2013/0197298 A1* | 8/2013 | Miller | H04R 25/00 600/25 |
| 2014/0114193 A1 | 4/2014 | Anthony et al. | |
| 2014/0148699 A1* | 5/2014 | Shim | A61B 8/488 600/441 |
| 2014/0330122 A1* | 11/2014 | Baghani | A61B 8/463 600/438 |
| 2016/0213350 A1* | 7/2016 | Lee | A61B 8/4483 |
| 2017/0014098 A1 | 1/2017 | Shao et al. | |
| 2017/0095228 A1 | 4/2017 | Richard | |
| 2017/0245834 A1 | 8/2017 | Takeda | |
| 2019/0192119 A1* | 6/2019 | Salcudean | A61B 8/4218 |

FOREIGN PATENT DOCUMENTS

| | | |
|---|---|---|
| EP | 3 095 387 A1 | 11/2016 |
| JP | 2005-144155 A | 6/2005 |
| JP | 2005-534455 A | 11/2005 |
| JP | 2010-227562 A | 10/2010 |
| WO | WO 00/55616 A1 | 9/2000 |
| WO | WO 2004/016176 A2 | 2/2004 |

OTHER PUBLICATIONS

Shung, "Diagnostic Ultrasound: Imaging and Blood Flow Measurements" 2nd edition, 2015 (Year: 2015).*
Winberg et al., "Inertial Mass Actuators, Understanding and Tuning" Eleventh International Congress on Sound and Vibration 2004, pp. 331-338 (Year: 2004).*
Ferraioli, G., et al., "WFUMB Guidelines and Recommendations for Clinical Use of Ultrasound Elastography Part 3: Liver," Ultrasound in Med. & Biol., pp. 1-19, 2015.
International Search Report as issued in International Patent Application No. PCT/EP2017/077417, dated Feb. 27, 2018.
Sandrin, L., et al., "Shear Elasticity Probe for Soft Tissues with 1-D Transient Elastography," IEEE Transactions on Ultrasonics, Ferroelectrics, and Frequency Control, vol. 49, No. 4, Apr. 2002, pp. 436-446.
Mellema, D. C.,et al., "Probe Oscillation Shear Elastography (PROSE): A High Frame-Rate Method for Two-Dimensional Ultrasound Shear Wave Elastography," IEEE Transactions on Medical Imaging, vol. 35, No. 9, Sep. 2016, pp. 2098-2106.
Sandrin, L., et al., "Non-Invasive Assessment of Liver Fibrosis by Vibration-Controlled Transient Elastography (Fibroscan)" Sep. 2011, "Liver Biopsy" Chapter 19. (Year: 2011).
Gilbertson, Matthew Wright, "Handheld force-controlled ultrasound probe" 2010, Massachusetts Institute of Technology. Dept. of Mechanical Engineering (Year: 2010).
Nabavizadeh, A., et al., "Automated Compression Device for Viscoelasticity Imaging," IEEE Transactions on Biomedical Engineering, vol. 64, No. 7, Sep. 2016, XP011653910, pp. 1535-1546.
Notice of Reasons for Refusal as issued in Japanese Patent Application No. 2019-522366, dated Nov. 16, 2021.
Non-Final Office Action as issued in U.S. Appl. No. 16/498,162, dated Nov. 24, 2021.

* cited by examiner

Figure 1a

Prior Art

Figure 1b

Prior Art

PROBE FOR TRANSIENT ELASTOGRAPHY

CROSS REFERENCE TO RELATED APPLICATIONS

This application is the U.S. National Stage of PCT/EP2017/077417, filed Oct. 26, 2017, which in turn claims priority to European Patent Application No. 16196165.1 filed Oct. 28, 2016, the entire contents of all applications are incorporated herein by reference in their entireties.

TECHNICAL FIELD

The present application relates to a probe for a transient elastography device. An object of the invention is a probe that can be used for the measurement of the viscoelastic properties of a human or animal tissue, and especially the stiffness of the liver. Another object of the invention is a method for measuring the viscoelastic properties of a tissue with said probe.

PRIOR ART

Several liver affections can be tracked by monitoring the viscoelastic properties of the liver tissue. Chronic viral hepatitis, alcoholic and non-alcoholic fatty liver disease, autoimmune hepatitis, drug-induced liver injury, primary biliary cirrhosis are all responsible for a progressive change in the stiffness of the liver. In some cases this increase in stiffness, also called fibrosis, can lead to cirrhosis and liver failure with severe consequences for the patient.

One of the most reliable and efficient techniques to measure liver stiffness is transient elastography (see for example "WFUMB guidelines and recommendations for clinical use of ultrasound elastography part 3: liver" by G. Ferraioli et al. published in "Ultrasound in Med. And Biol.", 41, 5, 2015).

The applicant has developed and commercialized a device called Fibroscan® (see for example patents EP1169636 and EP1531733). This device measures the stiffness of the liver by using an elastography technique called "Vibration Controlled Transient Elastography" (VCTE) developed by the applicant.

In a VCTE application, the measure of the liver stiffness relies on the measure of a transient shear wave propagation speed inside the tissue.

In order to perform such a measurement, a particular probe has been developed. Said probe comprises at least an electrodynamical actuator and at least an ultrasound transducer mounted on the tip of the probe.

For example, in the Fibroscan® probe, the vibrator moves the ultrasound transducer and pushes it against the patient body. This pulsed movement generates a transient shear wave which propagates inside the liver. The displacement generated by the propagating shear wave is probed by sending high frequency ultrasound short pulses or shots inside the medium.

Figure 1A:
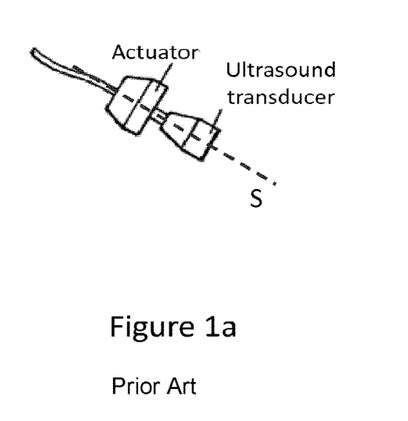
FIG. 1a shows a schematic representation of a VCTE probe according to the prior art.

Thanks to the advantageous geometry used by the Fibroscan® (see for example FIG. 1a) the mechanical actuator and the ultrasound transducer share the same symmetry axis, as indicated by the dashed line of FIG. 1a. This geometrical arrangement makes it possible to avoid systematic errors in the measurement of the shear wave propagation speed: the shear wave and the ultrasound shots propagate along the same direction.

Moreover, the Fibroscan® probe comes with a motion sensor capable of measuring the displacement of the probe tip with respect to the probe casing, for example a Hall effect position sensor. A measurement is validated only if the tip trajectory follows a predetermined profile, for example a period of sinusoid. In traditional VCTE probe only the relative movement of the probe tip with respect to the probe casing is measured. In other words, in a traditional VCTE probe the movement of the probe tip is measured in the reference frame of the probe casing.

A relevant problem in currently available VCTE probes is the control of the real movement of the probe tip when applying the transient shear wave to the tissue to be examined. For example, when the shear wave is applied, the recoil of the probe can add to the movement of the tip and the applied pulse can be deformed. This problem is related to the recoil of the operator's hand and to the control of the force which the operator has to apply in holding the probe against the patient's body: for a correct use of a VCTE probe according to the prior art a skilled or qualified operator is needed.

If the probe recoil is not controlled, the real movement of the tip of the probe with respect to the patient's body is unknown. The measurement can be dependent upon the force applied by the operator during the generation of the shear wave.

Figure 1B:
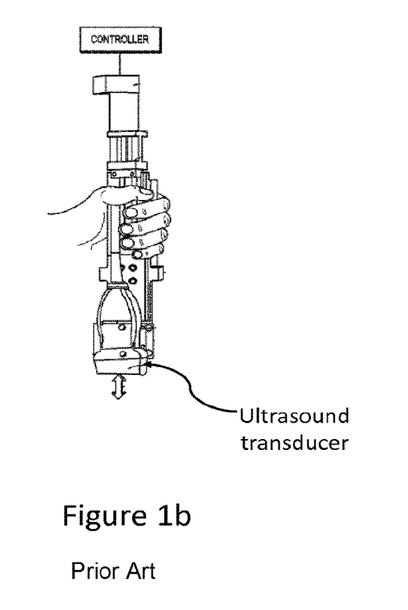
FIG. 1b shows a schematic representation of a force controlled ultrasound probe according to the prior art.

An ultrasound probe comprising a linear actuator and a force sensor is disclosed by patent applications U.S. Pat. No. 8,333,704 B2 ("Hand-held force-controlled ultrasound probe" filed by Anthony et al. on Dec. 18, 2010) and US 2012/0316407 A1 ("Sonographer fatigue monitoring" filed by Anthony et al. on Jun. 12, 2012). FIG. 1b illustrates the device described by the document U.S. Pat. No. 8,333,704. According to these documents, the ultrasound transducer is moved by an electrodynamical actuator in order to control the force applied against the tissue to be analyzed. The movement of the ultrasound transducer is controlled based on the signal provided by the force sensor and used as a feedback signal.

These documents solve the problem of applying a constant or a time-dependent force during an ultrasound measurement but the disclosed technical solutions have several drawbacks.

For example these devices described in the prior art comprise an external mechanical mobile part: as it is shown by the arrow in FIG. 1b the ultrasound transducer is moved with respect to the probe casing. Several drawbacks are associated to this external moving part, for example the need for frequent calibration operation.

Another solution described in the prior art is described in the document "Probe Oscillation Shear Elastography (PROSE): A high Frame-Rate Method for Two-dimensional ultrasound shear wave elastography" by D. Mellema et al. (published in IEEE Transaction on medical imaging, Vol. 35, No 9, September 2016). In this case a probe for continuous wave elastography is described. This solution is not adapted for the application of a transient shear pulse to the tissue but only for continuous wave shear wave oscillation. Moreover the described elastography probe is formed by two separate components, which is a severe drawback for the in-vivo applications. For example the described probe is difficult to manipulate due to the presence of several parts.

TECHNICAL PROBLEM

The present invention aims to at least partially solve the previous technical problems by proposing a VCTE probe which can be easily used by an operator, even without a specific preparation or training. Moreover, the probe according to the invention does not need frequent mechanical calibrations.

SUMMARY OF THE INVENTION

The VCTE probe described by the present application controls the real movement of the ultrasound transducer, i.e. the real shape of the pulse applied to the patient body during the application of the shear wave, without needing external mechanical mobile parts.

To this effect, an aspect of the invention is a probe for transient elastography comprising: a probe casing; at least one ultrasound transducer having a symmetry axis; at least a vibrator, said vibrator being located inside the probe casing; the vibrator is arranged to induce a movement of the probe casing along a predefined axis, the predefined axis being the symmetry axis of the ultrasound transducer; the ultrasound transducer is bound to the probe casing with no motion of the ultrasound transducer with respect to the probe casing.

A probe casing is the enclosure of the VCTE probe, said enclosure containing a vibrator or electrodynamical actuator. The probe casing can contain also other elements as a position sensor, logic circuits or connecting means in order to store data or exchanging data with a computer or other electronic devices. An ultrasound transducer is a device adapted to emit and receive ultrasound waves. It is formed by a single transducer or by an array of transducers, forming for example a linear detector.

A symmetry axis of the ultrasound transducer is an axis of geometrical symmetry of the transducer. The symmetry axis of the ultrasound transducer is also the direction along which the ultrasounds are emitted by the transducer. The symmetry axis of the transducer identifies the propagation direction of the ultrasound short pulses emitted by the transducer.

According to the present invention, the ultrasound transducer is bound in motion to the probe casing, which means that there is no relative movement of the ultrasound transducer with respect to the probe casing.

An extremity of the ultrasound transducer can be fixed to an extremity of the probe casing. Another extremity of the ultrasound transducer is free to vibrate in order to transmit the ultrasound waves to the medium to analyze.

Alternatively, the ultrasound transducer can be attached to the probe casing by means of a probe tip. When present, the probe tip has an extremity fixed to one extremity of the probe casing and another extremity fixed to the ultrasound transducer.

The explication of the invention given in the following paragraphs holds both when the ultrasound transducer is fixed directly to the probe casing and when the ultrasound transducer is fixed to the probe casing through a probe tip. These two configurations are given only as exemplary embodiments and other configurations are possible.

A vibrator is a device adapted to move a mass inside a probe casing. For example the vibrator can oscillate a mass at a frequency comprised between 1 and 5000 Hz.

The probe according to the invention can be considered as an inertial probe because the movement of the probe itself is generated by the movement of a mass inside the probe casing. The probe according to the invention comprises no external mechanical moving part.

The probe according to the invention is a transient elastography probe. This means that it is adapted to both applying a transient shear wave to the tissue to detect and analyze the propagation of the shear wave by sending ultrasound short pulses at high repetition rate.

The shear wave is generated in the tissue by the movement of the probe, which pushes the ultrasound transducer against the tissue itself. The shear wave is generated by applying a low frequency pulse to the surface of the medium. For example, the pulse can have the shape of one period of a sinusoid at a central frequency f comprised between 1 Hz and 5000 Hz.

The duration of the low frequency pulse applied to the tissue is comprised between $\frac{1}{2}f$ and $20/f$.

Ultrasound short pulses are emitted at a repetition rate comprised between 100 Hz and $100*10^3$ Hz.

The propagation of the shear wave is detected by sending ultrasound pulses or shots at high repetition rate inside the medium and by detecting the backscattered ultrasound signals. In fact the tissue contains inhomogeneity or particles capable of partially reflecting the ultrasound pulses.

By recording and analyzing subsequent backscattered signals it is possible to compute the displacement of the tissue due to the propagation of the shear wave. The properties of the shear wave can then be deduced. For example, the propagation speed of the shear wave is directly related to the stiffness of the viscoelastic medium.

An advantage of the probe described in the present invention is to control the real movement of ultrasound transducer. In fact, the ultrasound transducer is bound to the probe casing and there is no reciprocal movement between the ultrasound transducer and the probe casing. It is then possible to monitor the movement of the probe casing, which corresponds to the real movement of the ultrasound transducer. Measuring the real movement of the ultrasound transducer is important in order to control the shape of the transient shear wave generated inside the tissue. For example the movement of the probe can be measured with an accelerometer mounted on the probe itself.

In other words, according to the present invention, the movement of the ultrasound transducer is measured in the reference frame of the earth, in contrast to what is done in a traditional VCTE probe. In fact in a VCTE probe according to the prior art, the movement of the ultrasound transducer is measured in the reference frame of the probe casing and only the relative movement of the ultrasound transducer with respect to the probe casing is measured.

In practice, the motion of the mass actuated by the vibrator inside the probe casing can be determined by a control loop using the movement of the probe casing as a feedback signal. This makes it possible to directly compensate the motion of the hand of the operator during the application of the shear wave.

There is no need for the operator to apply a precise force in order to compensate the recoil of the probe. As a consequence, performing a measure of stiffness on a viscoelastic medium becomes easier for the operator of the probe. Moreover, the measured values of stiffness are more reproducible.

By measuring only the relative movement of ultrasound transducer with respect to the probe casing, as it is done in the prior art, it would not be possible to take on account the recoil of the probe. As a consequence, even if the relative movement of the tip follows a sinusoidal trajectory, the effective low frequency pulse applied to the patient body can have a different shape due to the recoil of the probe.

According to the present invention the ultrasound transducer in contact with the patient's body moves together with the probe casing. Detecting the probe casing movement is equivalent to detecting the probe tip movement. The probe casing movement is used as a feedback for the vibrator. In fact the amplitude of the oscillation of the vibrator can be adjusted in order to obtain the desired movement of the probe tip in contact with the patient's body. Moreover, the lack of external moving part in the probe according to the invention removes the need for frequent mechanical calibration.

Besides the main characteristics which have been outlined in the previous paragraphs, the inertial probe according to the invention may comprise one or more additional characteristics from those listed in the following, either individually or in any technical combination thereof:

- the ultrasound transducer is bound to the probe casing by means of a probe tip, said probe tip having a first extremity fixed to the probe casing and a second extremity fixed to the ultrasound transducer;
- the probe comprises at least a force sensor which is fixed to the probe casing, the force sensor being arranged to measure the deformation of the probe casing PC due to the contact with the tissue to be analyzed;
- the force sensor comprises a housing adapted to receive and secure the ultrasound transducer;
- the force sensor comprises a housing adapted to receive and secure the first extremity of the probe tip;
- the position sensor is coupled to the probe casing, the position sensor is arranged to measure the displacement of the inertial probe;
- the force sensor comprises at least a strain gauge and/or at least a strain sensing resistor;
- the at least one ultrasound transducer is interchangeable;
- at least one ultrasound transducer is a disk shape ultrasound transducer;
- the vibrator comprises at least an electrodynamic actuator comprising a part fixed to the probe casing and a mobile part;
- the mass of the mobile part of the vibrator is equal or greater than one fourth of the total mass M of the inertial probe;
- the position of the probe casing measured by the position sensor is used as a feedback signal in order to control the movement of the vibrator inside the probe casing;
- the low frequency pulse applied to the viscoelastic medium has a temporal duration comprised between ½f and 20/f, f being the central frequency of the pulse comprised between 1 Hz and 5000 Hz;
- the ultrasound short pulses are emitted at a repetition rate comprised between 100 Hz and 100000 Hz.

Another aspect of the present invention is a method for the use of the inertial elastography probe. Said method comprises at least one of the following steps:

- placing the probe in order to keep the ultrasound transducer in contact with viscoelastic medium to analyze and/or with the patient's body;
- triggering the application of the low frequency pulse for generating a shear wave inside the viscoelastic medium to analyze;
- emitting ultrasound shots inside the medium and recording the backscattered ultrasound signals;
- analyzing the recorded backscattered ultrasound signals in order to determine the displacement of the viscoelastic medium subjected to the propagation of the shear wave;
- based on the calculated displacement determine at least one viscoelastic parameter of the medium to analyze.

The step of triggering the application of the low frequency pulse is initiated manually by the operator or is conditioned on the verification of a verticality condition between the symmetry axis of the ultrasound transducer and the surface of the viscoelastic medium or the surface of the patient's body. For example, the angle between the symmetry axis of the ultrasound transducer and the normal to the surface of the viscoelastic medium is comprised between 0° and 30°.

The step of triggering the application of the low frequency pulse is realized if the force exerted by the probe on the viscoelastic medium is comprised between a low threshold and a high threshold. For example, the low threshold is comprised between 0.1 N and 5 N and the high threshold is comprised between 6 and 20 N.

LIST OF FIGURES

Other characteristics and advantages of the invention will be evident from the description thereof that is provided in the following, purely for non-limiting, exemplary purposes, with reference to the accompanying drawing, in which.

DETAILED DESCRIPTION OF THE INVENTION

Figure 2:
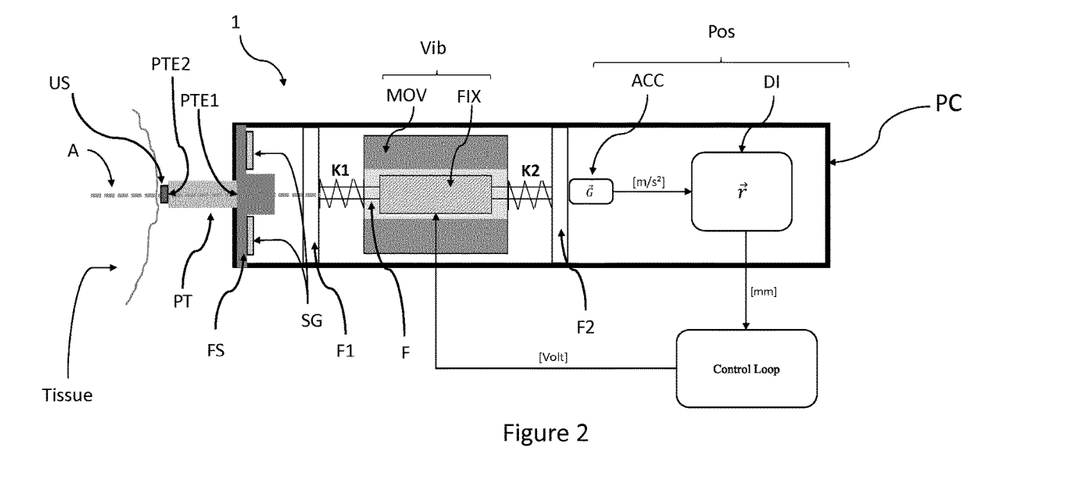
FIG. 2 shows a schematic representation of the transient elastography probe according to the present invention.

The probe 1 according to the present invention is represented in FIG. 2.

The probe 1 comprises:

- a probe casing PC containing at least a vibrator VIB comprising a fixed part FIX and a mobile part MOV;
- an ultrasound transducer US having a symmetry axis A;
- a position sensor POS comprising an accelerometer ACC and configured to measure the position or the displacement of the probe casing PC as a function of time, said position sensor cooperating with a control loop analyzing the data provided by the position sensor POS and controlling the vibrator VIB;
- a probe tip PT having a first extremity PTE1 fixed to the front end of the probe casing PC and a second extremity PTE2 fixed to the ultrasound transducer US, the front end of the probe casing PC being the extremity of the probe casing which is placed at proximity of the tissue;
- a force sensor FS placed at the front end of the probe casing, said force sensor providing an housing HOU for receiving and securing the ultrasound transducer US or the probe tip PT;
- connecting means for connecting the position sensor POS to the control loop and to the vibrator VIB.

The probe (1) showed in FIG. 2 further comprises:

a first vertical bar F1, a second vertical bar F2 and a horizontal bar F configured to fix the fixed part FIX of the vibrator VIB to the probe casing PC;

a first spring K1 extending from the first bar F1 to the mobile part MOV and a second spring K2 extending from the second bar F2 to the mobile part MOV;

at least a strain gauge or a strain resistor sensor SG mounted on the force sensor FS and configured to monitor the deformation of the probe casing PC by measuring the deformation of the force sensor FS, said deformation being caused by the contact between the ultrasound sensor US and the tissue to be analyzed.

According to an embodiment, the probe casing PC has a cylindrical shape, the axis A being the axis of the cylinder. Alternatively, the probe casing can have the shape of a solid of revolution having axis A.

The size of the probe casing is chosen in order to obtain a handheld probe. According to the embodiment the circumference of the cylinder is comprised between 120 mm and 160 mm.

The axis A is the symmetry axis of the ultrasound transducer US. For example in the case of a cylindrical ultrasound transducer the axis A is the axis of the cylinder forming the transducer. The axis A identifies also the propagation direction of the ultrasound short pulses emitted by the ultrasound transducer US.

According to another embodiment, the probe casing PC can have any shape adapted to be held by the operator's hand during the measurement. For example the probe casing PC can have the shape of a standard echography probe as it is showed in FIG. 5.

The vibrator VIB is placed inside the probe casing PC and it is formed by two elements: a mobile mass MOV and a fixed element FIX. The vibrator VIB is configured to set the mass MOV in motion, which generates the motion of the whole probe 1 along the axis A.

We define as vertical a direction normal to the axis A and as horizontal a direction parallel to the axis A.

According to an embodiment, the fixed part FIX is held in place by the holding means formed by a first vertical bar F1, a horizontal support bar F and a second vertical bar F2. The first and second vertical bars F1 and F2 are fixed to the probe casing. The horizontal support bar F extends from the first vertical bar F1 to the second vertical bar F2.

Alternatively, only one vertical bar, F1 or F2, can be present in order to support the horizontal bar F and the vibrator VIB.

The holding means F1, F and F2 block the fixed part FIX that is then bound to the probe casing PC. Any other configuration of holding means adapted to bind the fixed part FIX of the vibrator VIB to the probe casing PC can be used.

The mobile part MOV is separated from the first and second vertical bars, respectively F1 and F2, by two springs, respectively K1 and K2. The first spring K1 extends from the first vertical bar F1 to the moving part MOV, the second spring extends from the second vertical bar F2 to the moving part MOV.

When actuated by the vibrator VIB, the moving part MOV slides along the horizontal bar F. The horizontal bar F supports both the fixed part FIX and the mobile part MOV of the vibrator VIB.

The two springs K1 and K2 support the moving part MOV and act as a recalling force when the moving part MOV is set in motion.

It is worth to note that the moving part MOV oscillates inside the probe casing PC. The vibrator VIB does not move any external part of the inertial probe 1.

According to the embodiment represented in FIG. 2, the mobile mass MOV is a permanent magnet and the fixed part FIX is a coil. When an electric potential is applied to the coil FIX, a force is exerted between the coil FIX and the magnet MOV and an oscillation of the mass MOV along the axis A is produced.

The movement of the probe casing PC is induced by the movement of the moving part MOV due to both the action of the electromagnetic force between the coil and the magnet and the recalling force exerted by the springs K1 and K2. This movement can be described as consequence of the law of conservation of momentum, the movement of the moving part MOV determining the recoil of the probe casing PC.

As a result, the whole inertial probe 1 is set in motion and the ultrasound transducer US is pushed against the patient's body.

An advantage of this configuration is that the movement of the ultrasound transducer US against the tissue to analyze is directly determined by the vibrator VIB and it can be accurately controlled. In other words, given the absence of relative movement of the ultrasound transducer US with respect to the probe casing PC, the amplitude of the displacement of the ultrasound transducer US coincides with the amplitude of the movement of the probe casing PC. The shape of the low frequency pulse applied to the tissue is then accurately controlled.

According to the invention, there are several possible solutions to fix the ultrasound transducer US to the probe casing PC.

According to an embodiment, the ultrasound transducer US can be directly fixed to the probe casing PC. Alternatively the ultrasound transducer US can be fixed to a force sensor FS which is in turn attached to the probe casing PC.

An advantage of this embodiment is that this configuration is simple to realize. Moreover the force sensor FS is directly in contact with the ultrasound transducer US, which makes the detection of the probe casing PC deformation more efficient. The deformation of the probe casing PC is a micrometric deformation and it is due to the contact between the ultrasound transducer US and the tissue to be analyzed.

According to the embodiment represented in FIG. 2, the ultrasound transducer US is fixed to a probe tip PT which comprises a first extremity PTE1. The first extremity PTE1 is fixed to the front end of the probe casing PC. For example the probe tip PT has a sensibly cylindrical shape as it is shown in FIG. 1.

For example, the probe tip PT can be secured to the probe casing PC by inserting the first extremity of the probe tip PTE1 inside a housing HOU present in the force sensor FS, as it is showed in FIG. 2. The second extremity of the probe tip PTE2 is fixed to the ultrasound transducer US.

An advantage of this embodiment is that the probe tip PT is easily interchangeable. In other words it is possible to use different probe tips PT having different ultrasound transducer US, in order to adapt the properties of the emitted ultrasound shots to the properties of the tissue or of the patient's body.

According to an embodiment, the motion of the inertial probe 1 is measured by means of a position sensor POS.

An advantage of this embodiment is the direct measurement of the amplitude of the movement of the probe casing PC, which is identical to the amplitude of the movement of the ultrasound transducer US. In fact according to the invention no movement of the ultrasound transducer US with respect to the probe casing PC is possible. In other words, the ultrasound transducer US is at rest in the reference frame of the probe casing PC.

In the embodiment represented in FIG. 2 the position sensor POS is formed by an accelerometer ACC and an electronic circuit DI performing a double temporal integration. The double integrator DI gives the position r of the probe starting from the measured acceleration.

Any electronic circuit capable of computing the position r from the measured acceleration can be used in the present invention.

Advantageously, the position sensor POS provides a direct measurement of the displacement of the ultrasound transducer US. In other words the position sensor POS directly measures the shape of the low-frequency pulse applied to the tissue in order to generate the transient shear wave inside the tissue.

The probe 1 is then adapted to cooperate with a control loop capable of driving the vibrator VIB in order to obtain a predefined low frequency pulse shape. The control loop can for example be embedded in a Fibroscan® device.

The position r measured by the position sensor POS is then used as a feedback signal for controlling the vibrator VIB. According to an embodiment, the position r is fed to a control loop which controls the amplitude and frequency of the oscillation of the moving mass MOV.

Thanks to this arrangement, the movement of the ultrasound transducer US can be directly controlled and a well-defined low frequency pulse is applied to the patient's body.

According to the embodiment showed in FIG. 2 the probe 1 comprises also connecting means for transmitting the electrical signals between the position sensor POS, the control loop and the vibrator VIB. The connecting means comprise also means for delivering the electrical power necessary in order to operate the vibrator VIB, the ultrasound transducer US and the other embedded equipment. The power delivering means are not showed in FIG. 2.

According to an embodiment, the means connecting the position sensor POS, the control loop and the vibrator VIB can be wireless.

An advantage of the invention is the possibility to define and carefully control the low frequency pulse applied to the tissue. The real movement of the ultrasound transducer US is measured by the position sensor POS. The oscillation properties of the moving mass MOV are adjusted by the control loop in order to apply the target low frequency pulse shape to the patient's body.

In a typical transient elastography application, the low frequency pulse applied to the patient's body has a sinusoidal shape, with a central frequency comprised between 1 Hz and 5000 Hz, a peak-to-peak amplitude comprised between 10 µm and 20 mm and a duration comprised between 100 µs and 20 s. The repetition rate for the ultrasound pulses is comprised between 100 Hz and 100000 Hz.

According to an embodiment the peak-to-peak amplitude is comprised between 50 µm and 5 mm.

Figure 3:
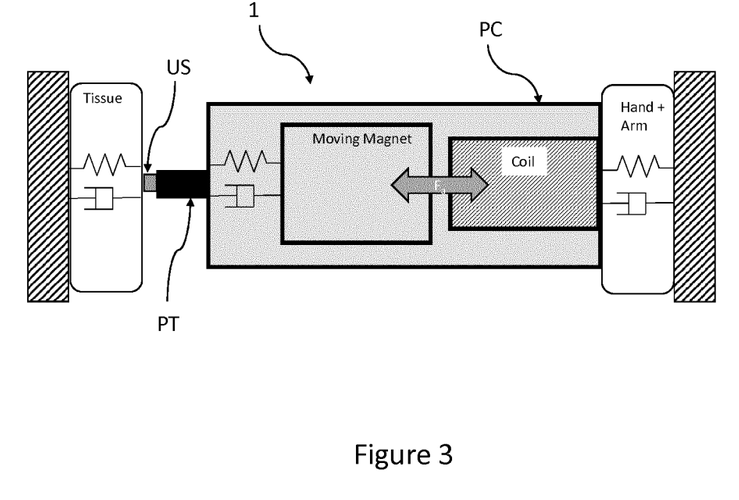
FIG. 3 shows a scheme of the mechanical coupling between the probe of FIG. 2, the tissue to be analyzed and the operator's hand.

FIG. 3 represents schematically the mechanical coupling between the probe 1, the tissue and the hand of the operator who holds the probe 1 in place.

The movement of the probe casing PC is transmitted to the tissue by pushing the transducer US against the tissue. The determination of the real movement of the US transducer against tissue is difficult due to the fact that the probe 1 is dynamically coupled also to the hand of the operator. The movement of the hand of the operator will unavoidably modify the shape of the low frequency pulse applied to the patient's body.

The present invention solves this problem by eliminating the movement of the ultrasound transducer US with respect to the probe casing PC and by measuring the position of the probe casing PC itself with a position sensor POS. The measured position is used as a feedback for the parameters of the vibrator VIB. The parameters of the vibrator VIB are then adjusted until the predefined low frequency pulse shape is obtained.

In other words, the probe 1 has no mechanical mobile external parts. The probe 1 is then an inertial probe, its movement being determined by the movement of a mass MOV placed inside the probe casing. Due to the absence of relative movement of the ultrasound transducer US with respect to the probe casing PC, measuring the amplitude of the displacement of the probe casing PC is equivalent to measuring the displacement of the ultrasound transducer US. The probe 1 is then able to directly measure the shape of the low-frequency pulse applied to the tissue and to compensate an eventual motion of the operator's hand. The absence of external moving part eliminates also the need for frequent mechanical calibration of the probe.

According to the embodiment showed in FIG. 2, the probe 1 comprises also a force sensor FS. The force sensor FS according to this embodiment is showed in FIG. 4a and FIG. 4b.

Figure 4A:
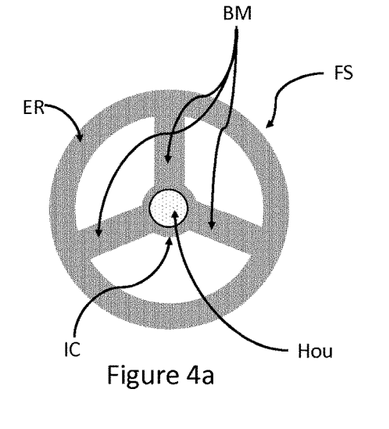
FIG. 4a shows the front panel of a force sensor, the force sensor being placed at the front end of the probe according to FIG. 2 and comprising a housing for an extremity of the probe tip.

FIG. 4a shows a first side of the force sensor FS to which the probe tip PT or the ultrasound transducer can be secured. The force sensor FS is placed at the front end of the probe casing PC. The force sensor FS comprises an external ring ER, an internal circle IC and three beams BM connecting the external ring ER to the internal circle IC. The internal circle IC comprises a cylindrical housing HOU configured to receive and secure an extremity of the probe tip PT.

Alternatively the ultrasound transducer US can be directly fixed to the force sensor FS when a probe tip PT is not used. In such a case a cylindrical or disk-shaped ultrasound transducer can be used.

The force sensor FS of FIG. 4a comprises also means to electrically connect the probe tip PT to the electrical circuits comprised in the probe 1. These connecting means are not shown in FIG. 4a.

In other words, when the first extremity PTE1 of the probe tip PT or the ultrasound transducer US is secured to the force sensor, the ultrasound transducer itself is connected, powered and ready to be used in a measurement.

An advantage of the force sensor FS is that the probe tip PT can be easily removed from its housing HOU and replaced with another probe tip PT holding a different ultrasound transducer US. This is advantageous for example when using the probe 1 in measuring the stiffness of the liver. In this case, depending on the characteristics of the patients, ultrasound transducers having different characteristics can be used. For example, in the case of an obese patient, it is useful to use an ultrasound transducer US having a greater penetration depth of the ultrasounds.

In other words, an interchangeable probe tip PT makes it possible to use ultrasound transducers US with different size/shape in order to adapt the ultrasound emission pattern to the patient's body.

Figure 4B:
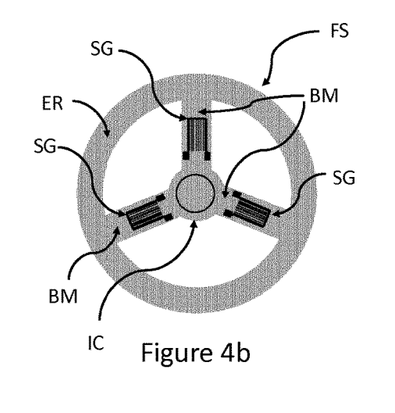
FIG. 4b shows the rear panel of the force sensor of FIG. 4a comprising three strain gauges.

FIG. 4b shows a second side of the force sensor FS, opposite to the side showed in FIG. 4a. At least one strain sensor is applied to this side of the force sensor FS.

The force sensor FS is fixed to both the probe casing and to the probe tip PT as it is showed in FIG. 2 bis. The force sensor FS is then mechanically coupled to both the US transducer and the probe casing PC.

The strain sensors SG are adapted to measure the micrometric deformation of the force sensor FS caused by the pressure applied on the ultrasound transducer US and on the probe tip PT when the probe is in contact with the tissue.

It is worth to note that micrometric deformations of the probe casing PC due to the pressure exerted against the patient's body are unavoidable. The present invention exploits this micrometric deformations in order to gather information on the verticality between the inertial probe 1 and the viscoelastic medium surface.

The verticality condition is verified when the axis A is substantially perpendicular to the surface of the viscoelastic medium. For example the verticality condition is met when the angle between the symmetry axis A and the normal to the surface of the viscoelastic medium is comprised between 0° and 30°.

According to an embodiment the force sensor FS comprises at least one strain gauge SG or a strain sensing resistor. Preferably three strain gauges SG or strain sensing resistors are used as it is showed in FIG. 4b. Each one of the three beams BM hosts a strain gauge SG or strain sensor. Two adjacent beams BM form an angle of 120°.

An advantage of this embodiment is to detect the direction along which the probe casing PC is deformed. This direction is related to the angle formed by the axis A and the surface of the tissue to be analyzed. In order to perform a reliable measure of the tissue stiffness, the axis A and the surface of the tissue must be almost perpendicular.

Thanks to the three strain gauges SG or other strain sensors, the operator has an information on the angle between the axis A and the surface of the patient's body and he can eventually correct this angle in order to obtain reliable stiffness measurements. When the verticality condition is not verified, the shear wave can be improperly applied to the patient's body. In this case the direction of propagation of the shear wave can be altered resulting in a wrong value of the measured stiffness.

The verticality condition is verified when the angle between the axis A and the normal to the surface of the viscoelastic medium is comprised between 0° and 30°. According to an embodiment the verticality condition is verified when the angle between the axis A and the surface of the viscoelastic medium is comprised between 0° and 20°.

According to the embodiment showed in FIG. 2, the vibrator VIB comprises at least a part FIX fixed to the probe casing PC and a moving part MOV. The moving part MOV being inside the probe casing PC, the inertial probe 1 has no mechanical external moving parts.

Thanks to this arrangement, it is possible to control the movement of the moving part MOV, for example by modifying the amplitude and frequency of its oscillation. By measuring the movement of the probe casing PC thanks to the position sensor POS it is then possible to accurately control the real movement of the probe tip PT.

For example, if the amplitude of the motion of the tip is too small, the control loop proceeds to modify the parameters of the vibrator VIB in order to increase the oscillation amplitude of the moving part MOV, which will result in an increase of the amplitude of the oscillation of the ultrasound transducer US.

Thanks to the feedback circuit comprising the position sensor POS and the control loop it is then possible to apply a low frequency pulse with a well-defined shape.

It is worth to note that the feedback circuit will automatically compensate any recoil or unintentional movement of the hand of the operator.

According to another embodiment of the present invention, the mass of the moving part MOV is equal or greater than one fourth of the total mass M of the inertial probe 1.

An advantage of this embodiment is to make it possible to effectively control the global movement of the inertial probe 1 by simply modifying the motion of the moving part MOV. In other words, if the mass of the moving part MOV was smaller its effect on the movement of the whole inertial probe 1 would be smaller, due to the momentum conservation law. The control of the motion of the tip would then be less efficient.

Figure 5:
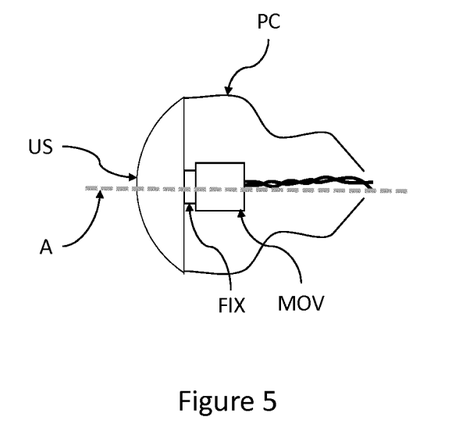
FIG. 5 shows another realization of the probe according to the invention.

FIG. 5 shows a version of the probe 1 obtained by modifying an echography probe. According to this embodiment, the fixed part FIX of the vibrator VIB is directly fixed to the wall of the probe casing PC, which is in this case the probe casing PC of an echography probe. As it is showed in FIG. 2, the axis A is the axis along which the moving part MOV oscillates. The ultrasound transducer US comprises in this case an array of single transducers emitting ultrasounds along the axis A.

According to the embodiment showed in FIG. 5, the probe casing PC can have a shape which is different from a cylinder or a solid of revolution. For example the probe casing PC can have the shape of any standard echography probe or simply have a shape that is adapted to being held in the hand of the operator.

According to the embodiment showed in FIG. 5 the vibrator VIB is fixed to one of the wall of the probe casing.

An advantage of this embodiment is to obtain an elastography probe according to the invention by modifying a standard echography probe.

According to an embodiment, the US transducer is a disk shape ultrasound transducer.

An advantage of this shape is to obtain a highly symmetric emission of the ultrasound shots. The high symmetric situation simplifies the calculation of the propagation both of the ultrasound shots and of the shear wave.

Another object of the present invention is a transient elastography method 100 for the measurement of the stiffness of a viscoelastic medium.

Figure 6:
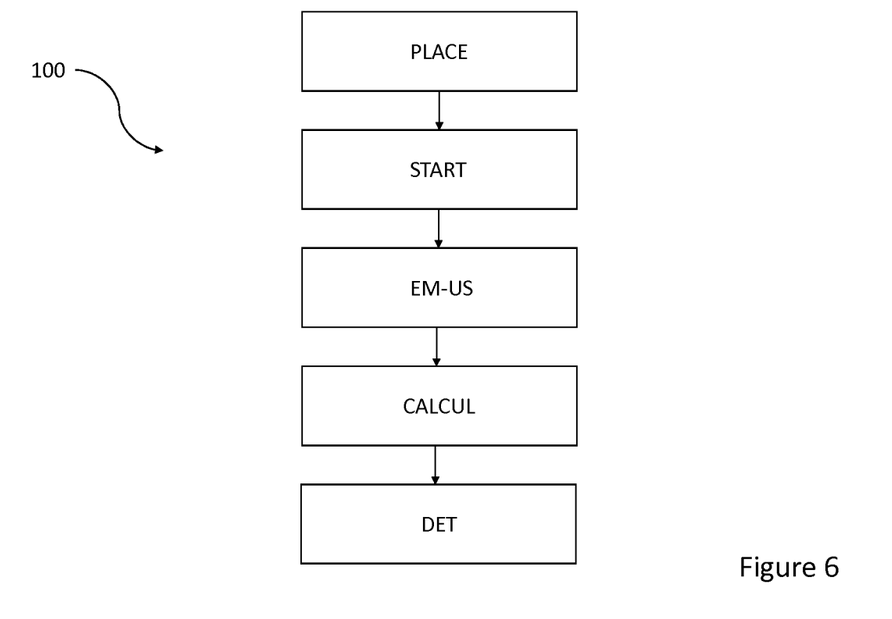
FIG. 6 shows the steps for implementing a transient elastography measure using the probe of FIG. 2 or FIG. 5.

FIG. 6 schematically shows the steps involved in the transient elastography method 100, said method using the probe 1.

According to an embodiment, the method 100 comprises a first step PLACE consisting in placing the ultrasound transducer US in contact with the viscoelastic medium.

Thanks to the inertial probe 1, this step does not require the application of a carefully determined force by the operator.

In other words, the operator does not need a particular training or a particular knowledge of the human body in order to use the inertial probe 1.

On the contrary, by means of the feedback mechanism provided by the position sensor POS and by the control loop and thanks to the absence of external moving part, the inertial probe 1 provides exactly the predetermined movement of the ultrasound transducer US. The movement of the tip is then used to apply a low frequency pulse to the medium for a transient elastography measurement.

If the angle formed between the axis A and the direction normal to the surface of viscoelastic medium exceeds a predetermined threshold, systematic errors in the measure of the stiffness occur. In other words, a verticality condition between the probe and the surface of the viscoelastic medium must be verified.

Thanks to the strain gauges SG placed on the force sensor FS at the front end of the probe casing PC, the verticality condition between the inertial probe 1 and the viscoelastic medium can be easily verified.

In other words, the inclination of the axis A with respect to the surface of the viscoelastic medium is effectively and easily controlled.

If the verticality condition is not verified, a signal is sent to the operator. The signal can be visual, sonorous or can have any other form that can be interpreted by the operator. This signal greatly simplify the search for the verticality condition performed by the operator.

When the verticality condition is verified, a shear wave is applied to the medium during the step START.

The application of the shear wave during the step START can be triggered automatically when the verticality condition is verified. According to a different embodiment the application of the shear wave can be triggered manually by the operator for example using a button or another triggering mechanism placed on the probe casing PC. Alternatively a remote trigger can be also used in combination with standard wireless connection means installed in the probe 1.

The triggering means are not showed in FIG. 2.

Moreover, also a condition on the force exerted between the transducer US and the surface of the tissue can be used. In this case, the low frequency pulse will be triggered only if the strength of the contact is comprised between two thresholds. The low threshold is comprised between 0.1 N and 5 N and the high threshold is comprised between 6 and 10 N.

In a transient elastography measurement, the low frequency pulse generates inside the viscoelastic medium a shear wave. The propagation of the shear wave is then probed by sending inside the medium high frequency ultrasound short pulses, also called ultrasound shots. The shear wave is applied by the ultrasound transducer US which pushes against the tissue due to the movement of the whole probe 1. The ultrasounds shots are emitted by the ultrasound transducer US.

The backscattered fraction of the ultrasound shots is recorded by the same ultrasound transducer US. In fact, due to the inhomogeneity of the viscoelastic medium, ultrasounds are scattered. A part of the scattered ultrasound signal travels back to the ultrasound transducer US and is recorded.

According to an embodiment, the emission of ultrasound shots and the recording of the backscattered signal begin simultaneously with the application of the shear wave.

According to another embodiment, the emission of the ultrasound shots and the recording of the backscattered signals are performed during the step EM-US, which begins when the probe tip PT has completed its movement in order to apply the shear wave to the tissue.

The displacement of the scattering particles inside the viscoelastic medium are calculated during the step CALCUL. For example, the calculation at this step is performed by means such as a microprocessor or other computing means.

The displacement of the scattering medium subject to the propagation of the shear wave can be calculated based on the backscattered ultrasonic signals.

For example, by correlating two backscattered ultrasound shots recorded at subsequent times it is possible to reconstruct the displacement of a scattering particle between the two considered times.

It is worth to note that the two subsequent backscattered ultrasound shots used in the correlation can also be nonconsecutive.

Several techniques of correlation between recorded backscattered signals are well known in the prior art, as cross-correlation or intercorrelation, sum of the squared differences or other. In general, any correlation technique can be used in order to determine the displacements of the viscoelastic medium subject to the propagation of the shear wave.

The step DET consists in determining at least one viscoelastic parameter of the viscoelastic medium. This is done starting from the displacements computed during the step CALCUL. For example the step DET is performed also by computing means such one or more microprocessors.

During the step DET viscoelastic parameters as elasticity, stiffness, viscosity, ultrasound attenuation, shear wave propagation speed or any combination thereof can be determined.

The invention claimed is:

1. A probe for transient elastography comprising:
   a probe casing;
   at least one ultrasound transducer having a symmetry axis;
   a vibrator located inside the probe casing,
   wherein:
     the at least one ultrasound transducer is bound to the probe casing with no motion of the at least one ultrasound transducer with respect to the probe casing;
     the vibrator is configured to induce a movement of the probe casing along the symmetry axis of the at least one ultrasound transducer, thereby inducing a corresponding movement of the at least one ultrasound transducer bound to the probe casing;
     the vibrator further is configured such that when the at least one ultrasound transducer is kept in contact with a patient's body, said corresponding movement applies a low frequency pulse that generates a transient shear wave in the patient's body;
     the probe further comprises a position sensor coupled to the probe casing, the position sensor being arranged to measure a displacement of the probe;
     the position sensor is in communication with a control loop circuitry such that the measured displacement of the probe is supplied as a feedback signal to the control loop circuitry that, based on the feedback signal, outputs a control signal that is adapted to drive the vibrator, the vibrator being adapted to receive the control signal output by the control loop circuitry to control a movement of the vibrator inside the probe casing and a shape of the low frequency pulse applied by the probe.

2. The probe for transient elastography according to claim 1, wherein the at least one ultrasound transducer is bound to the probe casing by means of a probe tip, said probe tip having a first extremity fixed to the probe casing and a second extremity fixed to the at least one ultrasound transducer.

3. The probe according to claim 1, further comprising a force sensor fixed to the probe casing, the force sensor being arranged to measure deformation of the probe casing due to the contact with the patient's body.

4. The probe according to claim 3, wherein the force sensor comprises a housing adapted to receive and secure the at least one ultrasound transducer.

5. The probe according to claim 3, wherein the at least one ultrasound transducer is bound to the probe casing by means of a probe tip, said probe tip having a first extremity fixed to the probe casing and a second extremity fixed to the at least one ultrasound transducer, and wherein the force sensor comprises a housing adapted to receive and secure the first extremity of the probe tip.

6. The probe according to claim 3, wherein the force sensor comprises at least a strain gauge and/or at least a strain sensing resistor.

7. The probe according to claim 1, wherein the at least one ultrasound transducer is interchangeable.

8. The probe according to claim 1, wherein the at least one ultrasound transducer is a disk shape ultrasound transducer.

9. The probe according to claim 1, wherein the vibrator comprises at least an electrodynamic actuator comprising a part fixed to the probe casing and a mobile part.

10. The probe according to claim 9, wherein a mass of the mobile part of the vibrator is greater than or equal to one fourth of a total mass of the probe.

11. A transient elastography method to measure a stiffness of a viscoelastic medium of a patient's body, the method comprising:
- placing the probe according to claim 1 such that the at least ultrasound transducer is kept in contact with a surface of the patient's body;
- triggering the probe to apply the low frequency pulse to generate a transient shear wave inside the viscoelastic medium; and
- emitting ultrasound shots into the viscoelastic medium and recording backscattered ultrasound signals thereof.

12. The transient elastography method according to claim 11, further comprising:
- analyzing the recorded backscattered ultrasound signals in order to determine a displacement of the viscoelastic medium due to a propagation of the transient shear wave;
- based on the calculated displacement, determining at least one viscoelastic parameter of the viscoelastic medium.

13. The transient elastography method according to claim 11, wherein said triggering the probe to apply the low frequency pulse is initiated manually by an operator or is conditioned on a verification of a verticality condition between the symmetry axis of the ultrasound transducer and the surface of the patient's body.

* * * * *